(12) United States Patent
Loy et al.

(10) Patent No.: US 8,758,731 B2
(45) Date of Patent: Jun. 24, 2014

(54) SKIN LIGHTENING BY TOPICAL APPLICATION OF 1-HYDROXYL 3,5-BIS(4'HYDROXYL STYRYL)BENZENE

(75) Inventors: Chong Jin Loy, Singapore (SG); Samantha Tucker Samaras, Long Valley, NJ (US); Michael D. Southall, Pennington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 81 days.

(21) Appl. No.: 13/538,054

(22) Filed: Jun. 29, 2012

(65) Prior Publication Data

US 2014/0004067 A1 Jan. 2, 2014

(51) Int. Cl.
*A61K 8/00* (2006.01)
*C07C 39/12* (2006.01)

(52) U.S. Cl.
USPC ............................................. 424/62; 568/717

(58) Field of Classification Search
USPC ........................................... 424/62; 568/717
See application file for complete search history.

(56) References Cited

U.S. PATENT DOCUMENTS

| | | | |
|---|---|---|---|
| 5,804,572 A | 9/1998 | Blank et al. | |
| 6,414,037 B1 | 7/2002 | Pezzuto et al. | |
| 6,653,327 B2 * | 11/2003 | Majeed et al. | 514/321 |
| 7,288,513 B2 | 10/2007 | Taylor et al. | |
| 7,745,670 B2 | 6/2010 | DiMauro | |
| 7,985,776 B2 | 7/2011 | Lilienfeld et al. | |
| 2008/0075671 A1 | 3/2008 | Di Mauro | |
| 2008/0076821 A1 | 3/2008 | Di Mauro | |
| 2009/0087385 A1 | 4/2009 | Di Mauro | |
| 2009/0325963 A1 | 12/2009 | Lilienfeld et al. | |
| 2010/0087527 A1 | 4/2010 | Di Mauro | |
| 2010/0292512 A1 | 11/2010 | DiMauro | |
| 2011/0081430 A1 | 4/2011 | Kaur et al. | |
| 2011/0081431 A1 | 4/2011 | Kaur et al. | |
| 2011/0081433 A1 | 4/2011 | Kaur et al. | |
| 2011/0257587 A1 | 10/2011 | Lilienfeld et al. | |
| 2012/0101156 A1 | 4/2012 | Oddos | |

FOREIGN PATENT DOCUMENTS

| | | | |
|---|---|---|---|
| KR | 2010-135577 | 12/2010 | |
| WO | WO 99/55352 | * 11/1999 | ............. A61K 35/78 |
| WO | 2007/080053 | 7/2007 | |

OTHER PUBLICATIONS

Ando et al., Quasi-Drugs Developed in Japan for the Prevention or Treatment of Hyperpigmentary Disorders, Int. J. Mol. Sci., 2010, 11 (2566-2575).
Chen, "SIRT1 Protects Against Microglia-dependent Amyloid-B toxicity Through Inhibiting NF-KB Signaling", J. Biol. Chem., (2005); vol. 280(48), pp. 40364-40374.
Handbook of Non-Invasive Methods and the Skin, eds. J. Serup, G. Jemec & G. Grove, Chapter 66.1 (2006) 579-582.
Kim, "Reservatrol Inhibits Inducible Nitric Oxide Synthase and Cycloozygenase-2 Expression in R-amyloid-treated C6 Glioma Cells"; Int. J. Mol. Med., (2006), vol. 17, pp. 1069-1075.
Solano et al., Hypopigmenting agents: an updated review on biological, chemical and clinical aspects, Pigment Cell Res. 19, 2006, (550-571).
Viniferol® Grapevine Shoot Extract for Cosmetics, Breko GmbH, 1977.
Zhang et al., "Hydrangeic acid from the processed leaves of Hydrangea macrophylla var. thunbergii as a new type of anti-diabetic compound", European Journal of Pharmacology, 606 (2009) 255-261.
Weber et al., Activation of NFkB is inhibited by curcumin and related enones. Bioorganic & Medicinal Chemistry 14 (2006) 2450-2461.
In re the USPTO U.S. Appl. No. 13/537,959 the non-final rejection dated Dec. 13, 2012.
In re the USPTO U.S. Appl. No. 13/537,959 the final rejection dated Mar. 27, 2013.
In re the USPTO U.S. Appl. No. 13/537,959 the Notice of Allowance dated Jul. 25, 2013.
In re the USPTO U.S. Appl. No. 13/538,017 the Restriction Requirement dated Apr. 29, 2013.
In re the USPTO U.S. Appl. No. 13/538,017 the non-final rejection dated Jun. 27, 2013.
In re the USPTO U.S. Appl. No. 13/538,101 the Restriction Requirement dated Apr. 26, 2013.
In re the USPTO U.S. Appl. No. 13/538,101 the non-final rejection dated Jul. 5, 2013.
CAS Registry No. 14938-35-3
Jang et al., "Inhibitory effects of curcuminoids from Curcuma longa on matrix metalloproteinase-1 expression in keratinocytes and fibroblasts", Journal of Pharmaceutical Investigation, Jan. 20, 2012.

* cited by examiner

*Primary Examiner* — Aradhana Sasan
(74) *Attorney, Agent, or Firm* — Sharon E. Hayner

(57) ABSTRACT

The present invention relates to compositions comprising 1-hydroxyl 3,5-bis(4'hydroxyl styryl)benzene or cosmetically acceptable salt thereof, and methods of lightening skin using said compositions.

9 Claims, No Drawings

SKIN LIGHTENING BY TOPICAL APPLICATION OF 1-HYDROXYL 3,5-BIS(4'HYDROXYL STYRYL)BENZENE

FIELD OF THE INVENTION

The invention relates to compositions and methods for the topical application of 1-hydroxyl 3,5-bis(4'hydroxyl styryl)benzene for skin lightening.

BACKGROUND OF THE INVENTION

It is known to apply anti-inflammatory compounds to the skin to provide anti-pigmentation benefits. A particular class of anti-inflammatory agents used for this purpose is agents that reduce the amount of melanin in melanocytes by means of inhibiting inflammatory mediator molecules. However, only a relatively small group of compounds have been identified as suitable for topical use to regulate melanin formation in skin.

SUMMARY OF THE INVENTION

The inventors have now surprisingly found that 1-hydroxyl 3,5-bis(4'hydroxyl styryl)benzene and cosmetically acceptable salts thereof are inhibitors of melanin formation in melanocytes and are suitable for topical application to skin, for example skin in need of skin lightening treatment.

The invention provides a method of lightening skin, comprising the step of topically applying to skin in need of skin lightening treatment a composition comprising 1-hydroxyl 3,5-bis(4'hydroxyl styryl)benzene or a cosmetically acceptable salt thereof.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Products described herein may optionally be in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin to lighten the skin as discussed infra. Such instructions may be printed on the container, label insert, or on any additional packaging.

As used herein, "topically applying" means directly laying on or spreading on outer skin, the scalp, or hair, e.g., by use of the hands or an applicator such as a wipe, mask (i.e., facial mask), roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, unless otherwise specified, all percentages of ingredients in compositions are weight percent of active/solids ingredient based on the total weight of composition.

Compositions of the present invention are suitable for treating human skin, e.g., skin on the face or body, to lighten the skin.

1-Hydroxyl 3,5-bis(4'hydroxyl styryl)benzene

Compositions of the present invention comprise 1-hydroxyl 3,5-bis(4'hydroxyl styryl)benzene or a cosmetically acceptable salt thereof.

1-Hydroxyl 3,5-bis(4'hydroxyl styryl)benzene is a curcumin analog having the structure below:

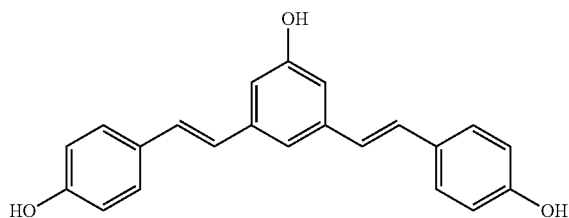 [SMILES: Oc1ccc(/C=C/c2cc(O)cc(/C=C/c3ccc(O)cc3)c2)cc1]

As described in U.S. Pat. No. 7,745,670,1-hydroxyl 3,5-bis(4'hydroxyl styryl)benzene can be made by reacting 1-(bromomethyl)-4-methoxybenzene with triethyl phosphate using an Arbuzov reaction to produce diethyl [(4-methoxyphenyl)methyl]phosphonate. This is coupled with 5-methoxybenzene-1,3-dicarbaldehyde-using sodium hydride as base in THF, followed by reaction with boron trichloride and dichloromethane to replace methoxy groups with hydroxyls.

Salts of 1-hydroxyl 3,5-bis(4'hydroxyl styryl)benzene can be made by, for example, reacting the 1-hydroxyl 3,5-bis (4'hydroxyl styryl)benzene with a base such as piperazine, or another base, to produce at least some phenoxide salt of 1-hydroxyl 3,5-bis(4'hydroxyl styryl)benzene.

Topical Compositions

Generally, the 1-hydroxyl 3,5-bis(4'hydroxyl styryl)benzene or salt thereof is present in the composition in a cosmetically effective amount, such as from about 0.01% to about 10%, preferably from about 0.1% to about 5%, more preferably from about 0.2% to about 2%, even more preferably from about 0.5% to about 1.5%, by weight of the composition.

The compositions of the present invention are applied topically to human skin and/or hair.

The compositions may be spreadable. They may be topically applied by spreading, for example spreading over the skin or hair, in particular over skin of the face or hands.

In one embodiment, a composition of the invention is topically applied without a voltage.

In addition to 1-hydroxyl 3,5-bis(4'hydroxyl styryl)benzene, the composition may further include a cosmetically acceptable topical carrier that may be from about 50% to about 99.99%, by weight, of the composition (e.g., from about 80% to about 99%, by weight, of the composition). In a preferred embodiment of the invention, the cosmetically acceptable topical carrier includes water.

The cosmetically acceptable topical carrier may be unsuitable for ingestion.

The cosmetically acceptable topical carrier may include an ingredient selected from one or more of the following five classes: wetting agents, emulsifiers, emollients, humectants, and fragrances. In certain embodiments, the cosmetically acceptable topical carrier includes ingredients from two or more of the above-mentioned classes, such as ingredients from at least three or more of such classes.

In one embodiment, the cosmetically acceptable topical carrier includes water, an emulsifier, and an emollient.

The compositions may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to solutions, suspensions, emulsions such as microemulsions and nanoemulsions, gels, solids and liposomes.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include humectants (e.g., water-retaining or hygroscopic materials) such as propylene glycol, pentylene glycol, polyethylene glycol, polypropylene glycol, glycerol, 1,2,4-butanetriol, sorbitol esters, 1,2,6-hexanetriol; as well as ethanol, and mixtures thereof. Solutions can optionally include a wetting agent, such as to provide foam, e.g, an anionic, non-ionic, or cationic wetting agent.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include hydrophobic compounds such as vegetable oils, mineral oils (e.g., petrolatum), fatty esters (e.g., isopropyl palmitate, c12-c15 alkyl benzoate) including those fatty esters of glycerol, silicone oils (e.g., dimethicone) and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Although it is preferred that the composition of the present invention includes water, the composition may alternatively be anhydrous or an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening thickening (gelling) agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic, cationic, and/or polymeric. Examples of suitable emulsifiers include those typically identified as such in the art of personal care and cosmetic formulations, e.g., cationic emulsifiers such as disteryldimonium chloride, non-ionic emulsifiers such as stereth-2, stereth-21; anionic emulsifiers such as potassium cetyl phosphate; polymeric emulsifiers such as acryloyldimethyltaurate/VP copolymers, and the like.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, (cross-linked) acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Active Agents

In one embodiment, the composition further contains another cosmetically active agent. As used herein, a "cosmetically active agent" is a compound (e.g., a synthetic compound or a compound isolated from a natural source or a natural extract) that has a cosmetic or therapeutic effect on the skin including, but not limiting to anti-aging actives, anti-inflammatory agents, tropoelastin promoters, anti-acne agents, anti-microbial agents, anti-inflammatory agents, anti-mycotic agents, external analgesics, sunscreens, antioxidants, keratolytic agents, vitamins, and skin firming agents.

In one embodiment, the composition includes an additional skin-lightening agent such as a tyrosinase inhibitor, melanin-degradation agent, melanosome transfer inhibiting agent including PAR-2 antagonists, retinoids, antioxidants, tranexamic acid, tranexamic acid cetyl ester hydrochloride, skin bleaching agent, linoleic acid, adenosine monophosphate disodium salt, Chamomilla extract, allantoin, opacifier, talc or silica, zinc salt, or the like, or other agent as described in Solano et al. Pigment Cell Res. 19 (550-571) and Ando et al. Int J Mol Sci 11 (2566-2575).

Examples of suitable tyrosinase inhibitors include but, are not limited to, vitamin C and its derivatives, vitamin E and its derivatives, kojic acid, arbutin, resorcinols, hydroquinone, flavones e.g., licorice flavanoids, licorice root extract, mulberry root extract, *dioscorea coposita* root extract, saxifraga extract and the like, ellagic acid, salicylates and derivatives, glucosamine and derivatives, fullerene, hinokitiol, dioic acid, acetyl glucosamine, 5,5'-dipropyl-biphenyl-2,2'-diol (magnolignan), 4-(4-hydroxyphenyl)-2-butanol (4-HPB), combinations of two or more thereof, and the like.

Examples of vitamin C derivatives include, but are not limited to, ascorbic acid and salts, ascorbic acid-2-glucoside, sodium ascorbyl phosphate, magnesium ascorbyl phosphate, and natural extract enriched in vitamin C.

Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives.

Examples of resorcinol derivatives include, but are not limited to, resorcinol, 4-substituted resorcinols like 4-alkyl-resorcinols such as 4-butyresorcinol (rucinol), 4-hexylresorcinol (SYNOVEA HR, SYNTHEON), phenylethyl resorcinol (SYMWHITE, SYMRISE), 1-(2,4-dihydroxyphenyl)-3-(2,4-dimethoxy-3-methylphenyl)-propane (nivitol, UNIGEN) and the like and natural extracts enriched in resorcinols.

Examples of salicylates include, but are not limited to, 4-methoxy potassium salicylate, salicylic acid, acetylsalicylic acid, 4-methoxysalicylic acid and their salts.

In certain preferred embodiments, the tyrosinase inhibitors include a 4-substituted resorcinol, a vitamin C derivative, or a vitamin E derivative. In more preferred embodiments, the tyrosinase inhibitor comprises phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents include PAR-2 antagonists such as soy trypsin inhibitor or Bowman-Birk Inhibitor, vitamin B3 and derivatives such as niacinamide, essential soy, whole soy, soy extract. In certain preferred embodiments, the melanosome transfer inhibiting agents includes a soy extract or niacinamide.

Examples of retinoids include, but are not limited to, retinol (vitamin A alcohol), retinal (vitamin A aldehyde), retinyl acetate, retinyl propionate, retinyl linoleate, retinoic acid, retinyl palmitate, isotretinoin, tazarotene, bexarotene, adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Other additional skin lightening agents include vitamin B5, vitamin B12, glycolic acid and extracts of *Paulownia* wood (for example the wood of *Paulownia tomentosa*, *Paulownia fortunei*, *Paulownia elongate*, *Paulownia taiwaniana*, and/or *Paulownia kawakamii*).

Examples of antioxidants include, but are not limited to, water-soluble antioxidants such as sulfhydryl compounds and their derivatives (e.g., sodium metabisulfite and N-acetylcysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, hesperedin, grape extract, portulaca extract, licochalcone, chalcone, 2,2'-dihydroxy chalcone, primula extract, propolis, and the like.

Other Materials

These include humectants, pH adjusters, chelating agents (e.g., EDTA), fragrances, dyes and preservatives (e.g., BHT, benzyl alcohol).

The composition and formulations and products containing such compositions of the present invention may be prepared using methodology that is well known by an artisan of ordinary skill.

Methods of Use

Compositions of the present invention may be topically applied to human skin that is in need of skin lightening treatment as described above. The compositions may be applied to the skin in need of such treatment according to a suitable treatment regimen, e.g., every month, every week, every other day, every day, twice a day, or the like.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

EXAMPLE 1

Melanogensis Inhibition Test

Ultraviolet (UV) radiation from the sun is the most important external stimulus for melanin formation leading to skin darkening. Reducing melanin formation in the skin may be achieved by inhibiting multiple steps of the melanin biogenesis process. Tyrosinase is the key regulatory enzyme of melanogenesis. Agents that inhibit tyrosinase will reduce melanin synthesis.

1-Hydroxyl 3,5-bis(4'hydroxyl styryl)benzene (0.0001, 0.001, and 0.01% w/v) was tested for tyrosinase inhibition as follows.

Mushroom tyrosinase samples (Sigma, T7755, 10 U/reaction) were treated with the samples of 1-hydroxyl 3,5-bis (4'hydroxyl styryl)benzene and control samples. Reaction was initiated by addition of 10 mM L-dopa (Research Organics, #2111D) at 37° C. Tyrosinase activity was measured by recording light absorption (optical density) at 492 nm after 30 min for both control samples (no exposure to test compound) and test samples that were exposed to the test compound.

Percent Inhibition of Tyrosinase was related to the reduction in absorption at 492 nm (relative to the control) by the following formula:

Percent Inhibition of Tyrosinase=[$T_{control}-T_{sample}$/$T_{control}$]*100 where $T_{control}$ is the tyrosinase activity of the control and $T_{sample}$ is the tyrosinase activity in the presence of test compound. Samples were tested in duplicate and Percent Inhibition of Tyrosinase was averaged and standard deviation was reported. The control had an average optical density of 0.622.

The results are provided in Table 1.

TABLE 1

| | Percent Inhibition of Tyrosinase activity (mean ± standard deviation) |
|---|---|
| 1-hydroxyl 3,5-bis(4'hydroxyl styryl)benzene - Free Phenol (0.0001%) | 3.3 ± 1.95 |
| 1-hydroxyl 3,5-bis(4'hydroxyl styryl)benzene - Free Phenol (0.001%) | 8.21 ± 1.27 |
| 1-hydroxyl 3,5-bis(4'hydroxyl styryl)benzene - Free Phenol (0.01%) | 11.84 ± 3.22 |
| 1-hydroxyl 3,5-bis(4'hydroxyl styryl)benzene - Piperazine salt (0.0001%) | 2.03 ± 3.94 |
| 1-hydroxyl 3,5-bis(4'hydroxyl styryl)benzene - Piperazine salt (0.001%) | 11.52 ± 3.16 |
| 1-hydroxyl 3,5-bis(4'hydroxyl styryl)benzene - Piperazine salt (0.01%) | 16.64 ± 2.76 |

1-hydroxyl 3,5-bis(4'hydroxyl styryl)benzene showed a substantial and dose dependent inhibition of tyrosinase enzyme activity.

EXAMPLE 2

Inhibition of UV-induced Melanogenesis

One or more samples of B16(F10) cells were prepared and each pre-treated with a test sample followed by UVB exposure as described below. Upon treatment, UVB stimulated melanogenesis in the cells and test compounds were evaluated based on their ability to inhibit or slow down the rate of melanogenesis. The cells were lysed for protein measurement at 595 nm and melanin content at 470 nm. The potency of the test compounds were determined by comparing the % inhibition achieved by the test compounds against the treated control.

On a first day, murine melanoma B16(F10) cells were seeded in 60 mm plates with a density of ~1 million cells per plate and incubated for 48 hrs at 37° C., 5% $CO_2$. On day 2, the cells with a confluency rate of 90-100% were treated with test compound at a predetermined concentration (e.g. 25 mg/mL) for two hours (for test compound samples only) followed by exposure to UVB 200 mJ/cm$^2$ (for test samples and treated control). The cells were harvested on day 3 (24 h post UVB irradiation for test samples and treated control) and lysed in protein lysis buffer (50 mM Tris, pH 8, 2 mM EDTA, 150 mM NaCl, and 1% TRITON X 100—a nonionic surfactant purchased from BioRad Cat.#: 161-0407), and centrifuged.

The resulting supernatant was mixed well with a protein dye assay (Bio-rad protein assay reagent) and a spectrophotometer (Molecular Devices VERSAmax) was used to determine the optical density (OD) of the sample at 595 nm, which was recorded as the "protein assay OD." The cell pellet remaining after removal of the supernatant was dissolved in alkaline DMSO buffer, and the resulting solution was similarly tested using a spectrophotometer for melanin absorbance assay at 470 nm. The absorbance was recorded as the "melanin assay OD."

Control samples of B16(F10) murine melanoma cells were prepared and harvested as indicated above, but without addition of any test sample and without exposure to UVB (untreated control). Other samples were prepared and harvested as indicated above, but without addition of test sample and exposed to UVB as described below (treated control).

Three samples each of the untreated control, treated control, and each test sample were made and the Melanin OD and Protein OD measured for each. The normalized melanin for each untreated control (3 samples), treated control (3 samples) and test sample (3 samples for each test compound) was calculated via the following equation:

Normalized Melanin=melanin assay *OD*/protein assay *OD*.

The averages of the Normalized Melanin of the untreated controls and treated controls were calculated (sum of the three calculated values/3).

The Induction value of the Control (which can be thought of as the UV-induced increase in melanin, without the benefit of any test sample to reduce melanogensis) was determined by subtracting the average Normalized Melanin of untreated control from the average Normalized Melanin of treated control. Similarly, the Induction value of each test sample (which can be thought of as the amount of additional melanin over and above the baseline of the sample not treated with UV) was then calculated by subtracting average Normalized Melanin of untreated control from the Normalized Melanin of the test sample. The Percent Inhibition for each test sample was then calculated via the equation:

Percent Inhibition=100×[(Induction value of Control−Induction value with Test Sample)/Induction value of Control].

The average Percent Inhibition was calculated as the sum of the three resulting Inhibition % values for each test sample divided by three.

The calculation sequence for Percent Inhibition are demonstrated using the example of 1-hydroxyl 3,5-bis(4'hydroxyl styryl)benzene—Free Phenol (0.0001%), in Table 2A, below.

TABLE 2A

Example Calculations of Percent Inhibition of UV-induced Melanogenesis

| | |
|---|---|
| Average Normalized Melanin Untreated control | 0.122 |
| Average Normalized Melanin UVB treated control | 0.234 |
| Induction value of control | 0.234 − 0.122 = 0.112 |
| Normalized Melanin value (duplicate test sample S1 & S2) | 0.19 (S1) <br> 0.187 (S2) |
| Induction value with Test sample | 0.19 − 0.122 = 0.068 <br> 0.187 − 0.122 = 0.065 |
| Percent Inhibition for Test sample | [(0.112 − 0.068)/0.112] × 100 = 39.05% (S1) <br> [(0.112 − 0.065)/0.112] × 100 = 41.93% (S2) <br> Ave = (39.05 + 41.93)/2 = 40.49% |

1-Hydroxyl 3,5-bis(4'hydroxyl styryl)benzene and its piperazine salt were evaluated according to the Inhibition of UV-induced Melanogenesis Test described above.

The results are reported in Table 2B.

TABLE 2B

Percent inhibition of UV-induced Melanogenesis

| | Percent inhibition of UV-induced melanogenesis (mean ± SD) |
|---|---|
| 1-hydroxyl 3,5-bis(4'hydroxyl styryl)benzene - Free Phenol (0.00001%) | 18.93 ± 5.92 |
| 1-hydroxyl 3,5-bis(4'hydroxyl styryl)benzene - Free Phenol (0.00005%) | 33.27 ± 4.39 |
| 1-hydroxyl 3,5-bis(4'hydroxyl styryl)benzene - Free Phenol (0.0001%) | 40.49 ± 2.04 |
| 1-hydroxyl 3,5-bis(4'hydroxyl styryl)benzene - Piperazine salt (0.00001%) | 13.93 ± 11.33 |
| 1-hydroxyl 3,5-bis(4'hydroxyl styryl)benzene - Piperazine salt (0.00005%) | 33.52 ± 1.54 |
| 1-hydroxyl 3,5-bis(4'hydroxyl styryl)benzene - Piperazine salt (0.0001%) | 55.70 ± 4.44 |

1-Hydroxyl 3,5-bis(4'hydroxyl styryl)benzene and its piperazine salt showed a strong inhibition in melanogenesis that was UV-induced.

EXAMPLE 3

Inhibition of Pigmentation

Skin epidermal equivalent tissues obtained from MatTek's MelanoDerm™ System were used as follows. MatTek's MelanoDerm™ System consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests.

1-Hydroxyl 3,5-bis(4'hydroxyl styryl)benzene and its piperazine salt were prepared in an appropriate vehicle and applied topically to the skin model daily. The experiment lasted for eight days. Measurement was taken on day 9.

The Degree of Lightness for each skin model tissue (L-Value) was measured using a spectrophotometer (Konica Minolta CM-2600d). The ΔL (degree of lightness as compared to vehicle-treated control) for each test sample was calculated using following formula:

ΔL=L-value of treated sample−L-value of control sample

The results are shown in Table 3.

TABLE 3

| | Degree of Lightness (ΔL) |
|---|---|
| 1-hydroxyl 3,5-bis(4'hydroxyl styryl)benzene - Piperazine salt (0.1%) | 1.46 ± 0.71 |
| 1-hydroxyl 3,5-bis(4'hydroxyl styryl)benzene - Piperazine salt (0.25%) | 2.83 ± 0.41 |
| 1-hydroxyl 3,5-bis(4'hydroxyl styryl)benzene - Piperazine salt (0.5%) | 4.60 ± 0.61 |
| 1-hydroxyl 3,5-bis(4'hydroxyl styryl)benzene - Free Phenol (0.5%) | 4.23 ± 0.64 |

1-Hydroxyl 3,5-bis(4'hydroxyl styryl)benzene and its piperazine salt showed inhibition in melanogenesis in epidermal equivalent tissues.

EXAMPLE 4

A composition according to the invention is prepared by blending the ingredients in Table 4.

TABLE 4

| Trade Name | INCI Name | % wt |
|---|---|---|
| Deionized Water | Water | 70.64 |
| Sodium Chloride | Sodium Chloride | 0.01 |
| | 1-hydroxyl 3,5-bis(4'-hydroxyl styryl)benzene | 1.00 |
| Snow White Petrolatum | Petrolatum | 4.00 |
| ISOFOL 28 | Dodecylhexadecanol | 2.50 |
| DOW CORNING Q7-9120 (20 CS) | Dimethicone | 1.25 |
| KESSCO IPP | Isopropyl Palmitate | 3.00 |
| VARISOFT TA-100 | Distearyldimonium Chloride | 5.00 |
| Glycerin | Glycerin | 12.00 |
| Benzyl Alcohol | Benzyl Alcohol | 0.60 |

Water is added to a process vessel. Mixing is begun and salt is added and mixed until dissolved. Heat is applied and mixing continued until to 85° C. is reached. 1-hydroxyl 3,5-bis(4'-hydroxyl styryl)benzene is solublized in glycerin, then added while mixing is continued and the temperature is maintained at 85° C. Distearyldimonium chloride is added, along with petrolatum and dodecylhexadecanol, dimethicone, and isopropyl palmitate. The composition is mixed at 85° C. for another 10-15 minutes. The composition is then removed from heat, mixed and cooled. At 40° C., benzyl alcohol is added, q.s. with water, mixed and cooled to 30-35° C. The composition is then filled into packaging.

A composition according to the invention is prepared by blending the ingredients in Table 5.

TABLE 5

| Trade Name | INCI Name | % wt |
| --- | --- | --- |
| Deionized Water | Water | 70.55 |
| Snow White Petrolatum | Petrolatum | 4.00 |
| ISOFOL 28 | Dodecylhexadecanol | 2.50 |
| DOW CORNING Q7-9120 (20 CS) | Dimethicone | 1.25 |
| BHT | BHT | 0.10 |
| KESSCO IPP | Isopropyl Palmitate | 3.00 |
| VARISOFT TA-100 | Distearyldimonium Chloride | 5.00 |
|  | 1-hydroxyl 3,5-bis(4'-hydroxyl styryl)benzene | 1.00 |
| Glycerin | Glycerin | 12.00 |
| Retinol 10S | *Glycine Soja* (Soybean) Oil and Retinol | 1.00 |
| Benzyl Alcohol | Benzyl Alcohol | 0.60 |

Water is added to a process vessel and the temperature is set to 85° C. Mixing is begun and glycerin is added and mixed until dissolved. VARISOFT TA-100 is added, along with petrolatum and ISOFOL 28, DOW CORNING Q7-9120 20 CS, and isopropyl palmitate. The composition is mixed at 85° C. for another 10-15 minutes. The composition is then removed from heat, mixed and cooled.

A composition according to the invention is prepared by blending the ingredients in Table 6.

TABLE 6

| Trade name | INCI name | % wt |
| --- | --- | --- |
| Deionized water | Water | 73 |
| HYDROLITE 5 | Pentylene glycol | 5 |
|  | 1-hydroxyl 3,5-bis(4'-hydroxyl styryl)benzene | 5 |
| NATRULON OSF | Carthamus Tinctorius Oleosome | 10 |
| FINSOLV TN | C12-15 Alkyl Benzoate | 4 |
| ARISTOFLEX AVC | Ammonium Acryloyldimethyltaurate/VP Copolymer | 2 |
| *Tanacetum parthenium* extract | Chrysanthemum Parthenium (Feverfew) Leaf/Flower/Stem Juice | 1 |

1-hydroxyl 3,5-bis(4'-hydroxyl styryl)benzene is weighed and dissolved in HYDROLITE 5 and deionized water is added to form Phase A. Oleosomes and FINSOLV TN are mixed to form Phase B. Phase B is added to Phase A very slowly under continuous mixing. Mixing is continued for 15 minutes until a uniform emulsion is formed. ARISTOFLEX AVC is added to the emulsion under continuous mixing at high speed to obtain a thick, smooth and homogenous formulation.

A composition according to the invention is prepared by blending the ingredients in Table 7.

TABLE 7

| Trade Name | INCI Name | % wt |
| --- | --- | --- |
| Deionized Water | Water | 67.70 |
| Carbomer | Cross-linked polyacrylic acid | 0.60 |
| VERSENE NA | Disodium EDTA | 0.20 |
| Brij 72 | Steareth-2 | 0.75 |
| Brij 721 | Steareth-21 | 1.50 |
| FINSOLV TN | C12-15 Alkyl Benzoate | 2.00 |
| Dimethicone | DOW CORNING Q7-9120 Silicone Fluid (20 cst) | 5.00 |
| PHENONIP XB | Phenoxyethanol, Methylparaben, Ethylparaben, Propylparaben | 1.00 |
| LYS'LASTINE | *Peucedanum graveolens* (10% active) | 10.00 |
| SYMMATRIX | Maltodextrin, *Rubus Fruticosus* (Blackberry) Leaf Extract (10% active) | 10.00 |
| 1-hydroxyl 3,5-bis(4'-hydroxyl styryl)benzene |  | 0.25 |
| Glycerin | Glycerin | 1.0 |

An oil phase is prepared by adding FINSOLV TN to a clean glass beaker. Agitation is begun and the vessel is heated to 55-60° C. When the oil phase reaches 55° C. or higher, Brij 72 and Brij 721 are added. When the oil phase reaches 55-60° C., it is held at that temperature and mixed for 15 min (or until uniform). The temperature is then held at 55-60° C. with mixing until addition to water phase.

A water phase is prepared by adding water to a clean glass beaker. Agitation is begun and the vessel is heated to 55-60° C. Disodium EDTA is added. At 55-60° C., the ingredients are mixed for 15 min or until homogeneous. The temperature is then held at 55-60° C. with mixing for phasing.

The oil phase is added to the water phase with increased agitation and then mixed at high speed for 10-20 min. At 50° C. or lower, dimethicone is added. At 40° C. or lower, PHENONIP XB is added. The phases are then mixed for 10 min or until uniform. Sodium hydroxide is added (target pH is 5.4). The composition is then mixed for 10 min or until uniform. LYS'LASTINE and SYMMATRIX are then added. 1-hydroxyl 3,5-bis(4'-hydroxyl styryl)benzene is weighed and dissolved in glycerin and added to the mixture, which is mixed until uniform. Water is then added to QS and the composition is mixed for 10 additional minutes.

It is understood that while the invention has been described in conjunction with the detailed description thereof, that the foregoing description is intended to illustrate and not limit the scope the invention, which is defined by the scope of the appended claims. Other aspects, advantages, and modifications are within the claims.

The invention claimed is:

1. A method of lightening skin, comprising the step of topically applying to skin in need of skin lightening treatment a composition comprising 1-hydroxyl 3,5-bis(4'hydroxyl styryl)benzene or a cosmetically acceptable salt thereof.

2. The method of claim 1, wherein the composition further comprises a cosmetically-acceptable topical carrier comprising an ingredient selected from the group consisting of wetting agents, emulsifiers, emollients, humectants, and fragrances.

3. The method of claim 2, wherein the cosmetically-acceptable topical carrier comprises ingredients selected from at least two of the following classes: wetting agents, emulsifiers, emollients, humectants, and fragrances.

4. The method of claim 2, wherein the cosmetically-acceptable topical carrier comprises an emollient and an emulsifier.

5. The method of claim 2, wherein the cosmetically-acceptable topical carrier comprises ingredients selected from at least three of the following classes: wetting agents, emulsifiers, emollients, humectants, and fragrances.

6. The method of claim 1, wherein the composition further comprises an additional skin-lightening agent.

7. The method of claim 1, wherein the composition comprises about 0.01% to about 10% of said 1-hydroxyl 3,5-bis (4'hydroxyl styryl)benzene or cosmetically acceptable salt thereof.

8. The method of claim 1, wherein the composition is applied using an applicator selected from the group consisting of masks and wipes.

9. The method of claim 1, wherein the composition comprises an additional skin lightening agent.

* * * * *